United States Patent
Miyai et al.

(10) Patent No.: US 7,071,468 B2
(45) Date of Patent: Jul. 4, 2006

(54) CIRCUIT PATTERN INSPECTION METHOD AND ITS APPARATUS

(75) Inventors: Hiroshi Miyai, Hitachi (JP); Ryuichi Funatsu, Hitachinaka (JP); Taku Ninomiya, Hitachinaka (JP); Yasuhiko Nara, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 10/957,748

(22) Filed: Oct. 5, 2004

(65) Prior Publication Data
US 2005/0109938 A1 May 26, 2005

(30) Foreign Application Priority Data
Oct. 8, 2003 (JP) .............................. 2003-348951

(51) Int. Cl.
*G01N 21/00* (2006.01)
(52) U.S. Cl. ...................... 250/310; 250/311; 250/307; 250/306; 382/149
(58) Field of Classification Search ..................... None
See application file for complete search history.

(56) References Cited

U.S. PATENT DOCUMENTS

2001/0033683 A1* 10/2001 Tanaka et al. .............. 382/149

2005/0146714 A1* 7/2005 Kitamura et al. ........ 356/237.2

FOREIGN PATENT DOCUMENTS

JP 2002-124555 4/2002
JP 2002-174603 6/2002

* cited by examiner

*Primary Examiner*—Nikita Wells
*Assistant Examiner*—Zia R. Hashmi
(74) *Attorney, Agent, or Firm*—McDermott Will & Emery LLP

(57) ABSTRACT

A circuit pattern inspection method and apparatus capable of readily setting an optimum threshold value while it is confirmed that a defect detected when a defect is checked can be detected at what threshold value and capable of forming a recipe easily. A circuit pattern inspection of irradiating an electron beam to a specimen formed with a circuit pattern on a surface thereof, forming an inspection image and a reference image in accordance with a secondary electron of a reflected electron from the specimen, and acquiring an abnormal portion from a difference between the inspection image and the reference image, wherein a plurality of characteristic quantities of the abnormal portion are obtained from an image of the abnormal portion, and the abnormal portion is selectively displayed by changing an inspection threshold value virtually set for the characteristic quantities.

6 Claims, 9 Drawing Sheets

CIRCUIT PATTERN INSPECTION METHOD AND ITS APPARATUS

BACKGROUND OF THE INVENTION

1. Field of the Invention

The present invention relates to inspection technologies for inspecting substrates having fine circuit patterns such as semiconductor products and liquid crystal products, and more particularly to an inspection method and apparatus for inspecting circuit patterns formed by using an electron beam.

2. Description of the Related Art

An inspection apparatus for inspecting semiconductor wafers will be described by way of example. Semiconductor devices are manufactured by repeating a process of transferring a pattern formed on a semiconductor wafer by a lithography process and an etching process. Defective patterns and foreign matters formed by the lithography process and etching process during the semiconductor device manufacture processes influence greatly the manufacture yield of semiconductor devices. It is therefore necessary to detect at an earlier stage or in advance the generation of abnormalities and defects.

A variety type of many defects exist at the leading stage and development stage of manufacture processes using semiconductor wafers. Since the causes of defects are different among the types of defects, different countermeasure methods and positions are used. It is difficult to countermeasure all defects at a time, and there are defects influencing together. It is therefore rare that one countermeasure becomes sufficient. If it can be confirmed that the number of particular defects reduces before and after a plurality of countermeasures, these countermeasures are effective. However, if a variety of many defects exist at the earlier stage, it is very difficult to find which defects among a number of detects are reduced by which countermeasure. Developers of manufacture processes have studied these defects and paid knowledge and labor in finding the optimum conditions of processes, and have relied largely upon the experience of those skilled in the art.

Known apparatuses for inspecting defects on a pattern on a semiconductor wafer include an optical inspecting apparatus which irradiates white light on a semiconductor wafer and compares similar circuit patterns on a plurality of LSIs by using optical images, an SEM type visual inspecting apparatus which detects secondary electrons and reflected electrons generated by irradiating an electron beam to obtain an image which is compared with a reference image, to thereby detect abnormalities such as defects and foreign matters, and other inspecting apparatuses. SEM is an abbreviate term for Scanning Electron Microscopy.

With these inspecting apparatuses, an inspected image is compared with a reference image, only the images having different gradation values obtained by binarizing a luminance are extracted to use them as the abnormal portions. Defect images are formed or the positions of the abnormal portions on the semiconductor wafer are displayed, to thereby display a plurality of defects for an operator. The operator transmits data of a defect distribution displayed as a defect map on the semiconductor wafer to another analyzing apparatus. The analyzing apparatus selects several defects from a plurality of defects and makes a detailed analysis by using an observation image obtained by irradiating an electron beam.

A defect map displays generally many defects having a variety type of defect causes, and the operator wishes to find that an analysis of which defect is most urgent. Practically, this has relied conventionally upon the skill of the operator. Defects extracted and displayed on a defect map indicate only the abnormal portion having a different image. Abnormal portions which are not defects are extracted in some cases, and a distribution of a variety type of defects on a semiconductor wafer is displayed without any discrimination among them.

From this viewpoint, it has been tried to make the inspection apparatus not only merely display a defect map, but also extract the defects unnecessary for a defect analysis and display only necessary defects as defect data. For example, the optical inspecting apparatus cannot detect non-conduction defects and electric short-circuits of a semiconductor device formed on a semiconductor wafer during a contact hole forming process. However, since the SEM visual inspecting apparatus can detect such non-conduction defects and short-circuits, it has been tried to discriminate between the non-conduction defects and the short-circuits from the defect image and the coordinate values of the defect on the semiconductor wafer (for example, refer to JP-A-2002-124555 (Page. 8, FIG. 6).

Although not pertaining to the manufacture processes for a semiconductor device, a method is know which classifies defects in accordance with a plurality of characteristic quantities such as the contour and luminance of each manufacture defect (for example, refer to JP-A-2002-174603 (Page. 3, FIG. 6). However, no specific description has been found which illustrates a method of eliminating unnecessary defects extracted with a SEM visual inspecting apparatus during the manufacture processes of semiconductor devices.

SUMMARY OF THE INVENTION

A variety type of many defects exist at the leading stage and development stage of manufacture processes for semiconductor wafers. Since the causes of defects are different among the types of defects, different countermeasure methods and positions are used. It is difficult to countermeasure all defects at a time, and there are defects influencing together. Therefore, a plurality of countermeasures is performed not at a time but in sequentially. In this case, it is necessary to confirm that the number of particular defects reduces before and after each countermeasure. Therefore, if a variety of many defects exist at the earlier stage, it takes a considerable labor in finding a small number of particular defects. Developers of manufacture processes have studied these defects and paid knowledge and labor in finding the optimum conditions of processes.

Since the value of a memory cell portion of a DRAM (Dynamic Random Access Memory) is required to be retained for a predetermined time, leak of contacts in the memory cell portion poses an important issue. On the other hand, in an SRAM (Static Random Access Memory), the leak is allowed to some degree in many cases, as compared to DRAM. As described above, in the inspection using an electron beam image, the contact leak portion is brighter than other portions because the contact leak portion has a low resistance to the substrate. Therefore, in the inspection of leak portions of SRAM, a variation in leak currents is detected as a defect. Namely, when a non-conduction defect is to be detected, a variation in leak currents is detected as a defect so that the non-conduction defect cannot be detected efficiently. If a foreign matter or the like exists while an electrically abnormal pattern is detected, a mixture of an electrically abnormal portion and a foreign matter is detected so that the electrically abnormal portion cannot be detected efficiently. The inspection efficiency can be improved by extracting the characteristics of each defect and automatically classifying the characteristics during the inspection. It is necessary to set the optimum classification conditions while a recipe for defining the inspection contents for the automatic classification is formed. However, in order to form the efficient classification conditions, there arises the problem that it takes a long time to form a recipe. Since the above-described classification conditions become the efficient conditions after repetition of inspections, it is necessary to allow the once formed classification conditions to be amended while the recipe is formed.

It is an object of the present invention to provide a circuit pattern inspection method and apparatus capable of readily setting an optimum threshold value while it is confirmed that a defect detected when a defect is checked can be detected at what threshold value and capable of forming a recipe easily.

In order to achieve the above object, an embodiment of the present invention provides a circuit pattern inspection of irradiating an electron beam to a specimen formed with a circuit pattern on a surface thereof, forming an inspection image and a reference image in accordance with a secondary electron of a reflected electron from the specimen, and acquiring an abnormal portion from a difference between the inspection image and the reference image, wherein a plurality of characteristic quantities of the abnormal portion are obtained from an image of the abnormal portion, and the abnormal portion is selectively displayed by changing an inspection threshold value virtually set for the characteristic quantities.

According to the present invention, it is possible to readily set an optimum threshold value while it is confirmed that a defect detected when a defect is checked can be detected at what threshold value and capable of forming a recipe easily.

Other objects, features and advantages of the invention will become apparent from the following description of the embodiments of the invention taken in conjunction with the accompanying drawings.

DESCRIPTION OF THE EMBODIMENTS

Embodiments of a circuit pattern inspection method and apparatus of this invention will be described in detail with reference to the accompanying drawings.

Figure 1:
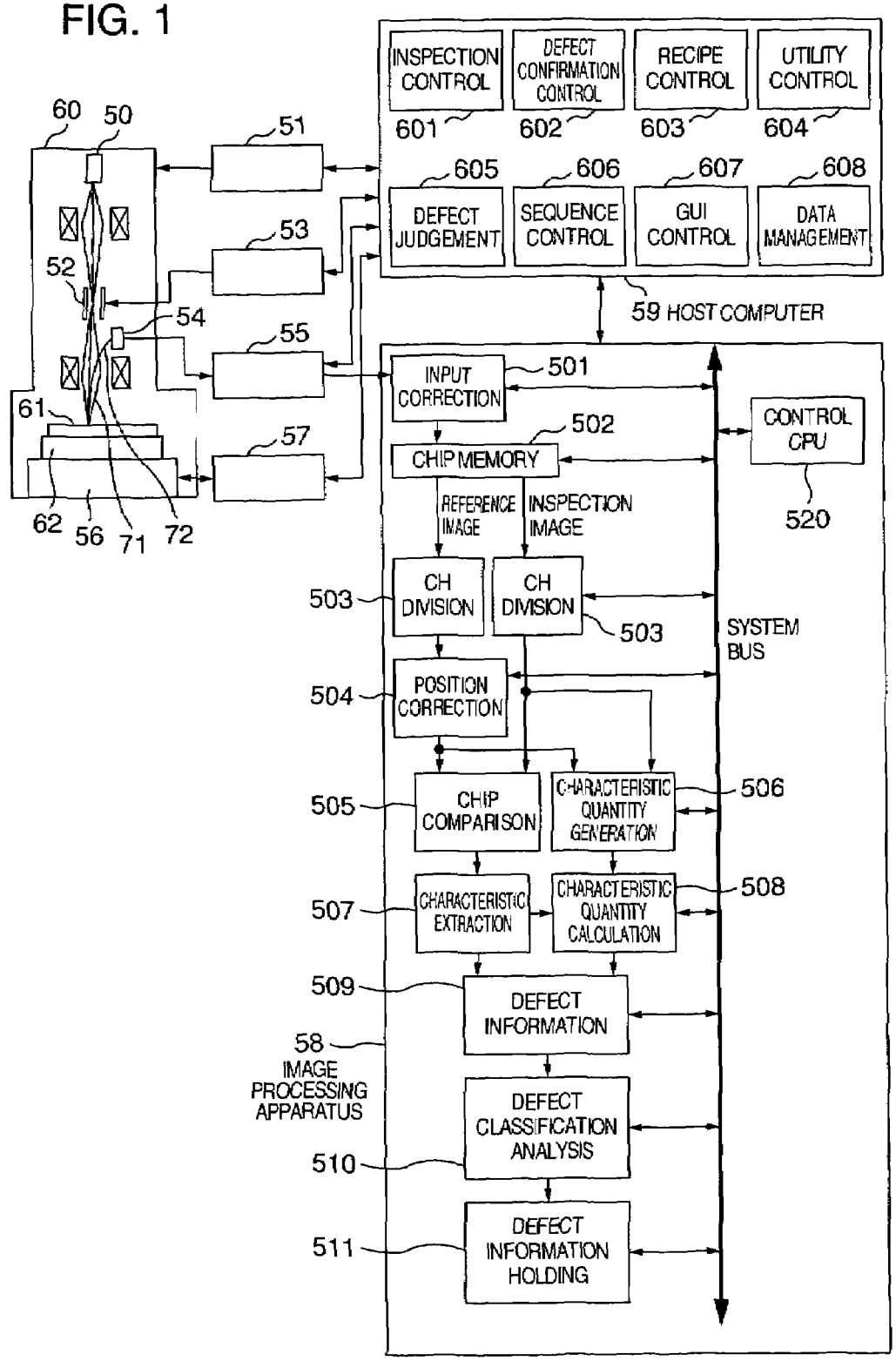
FIG. 1 is a functional block diagram showing the structure of an inspection apparatus.

FIG. 1 is a functional block diagram showing the structure of an inspection apparatus. The main portion of a SEM 60 is mainly constituted of an electron beam generation unit including an electron source 50 and the like, an electron beam scan control unit including a deflection electrode 52 and the like, and a specimen operation unit including a specimen 61, a specimen holder 62, a specimen moving stage 56 and the like.

A primary electron beam 71 generated by the electron source 50 is accelerated by an unrepresented acceleration electrode and irradiated to the specimen 61 held by the specimen holder 62. During this process, an electronic optical system constituted of a coil and an electrode is controlled by an electronic optical system control circuit 51 so that the electron beam 71 is focussed at a specimen position. The electron beam 71 is scanned by the deflection electrode 52 and a deflection control circuit 53 to acquire a stripe image, in combination with the specimen moving stage 56 controlled by a stage control circuit 57.

The primary electron beam 71 irradiated to the specimen 61 emits a secondary electron 72 from the specimen surface. This secondary electron 72 is again accelerated by an unrepresented electrode, and guided to a detector 54 by an unrepresented electrode. The secondary electron captured by the detector 54 is converted into an electric signal by a detector circuit 55 and sent to an image processing apparatus 58.

An image sent to the image processing apparatus 58 is corrected by an input correction unit 501. For example, correction includes a gradation conversion for adjusting the contrast of the image, dark level correction, a beam addition process and the like. The corrected image is sent to a chip memory 502. The chip memory 502 temporarily stores the image in a chip unit, and generates a delay image for image comparison. An inspection image and a reference image generated by the chip memory 502 are sent to a CH division unit 503 whereat they are classified into a plurality of channels (hereinafter abbreviated to CH). Since each image is divided into a plurality of CHs, the image process rate can be made lower than the image itself is processed.

For the image divided into CHs, a position displacement between the inspection image and reference image is measured and thereafter, a position correction unit 504 corrects the positions to make them the same in a pixel unit. The image after the correction is sent to a chip comparison unit 505 and a characteristic quantity generation unit 506. The chip comparison unit 505 extracts a different portion between the inspection image and reference image and outputs it as the image data representative of a defect. A different portion, that is an abnormal portion, between the inspection image and reference image is more accustomed if it is called a defect in the circuit pattern inspection. Therefore, in the following, the term defect is used where applicable as having the meaning equivalent to the abnormal portion.

The characteristic quantity generation unit 506 calculates, for example, a gradation difference between the inspection image and reference image and a gradient, i.e., differential value, of a gradation value of each pixel of the inspection image. The defect image is sent to a characteristic extraction unit 507 whereat the position, projection length, area and the like of the defect portion are obtained. A characteristic calculation unit 508 collects the gradation difference and differential value supplied from the characteristic quantity generation unit 506, synchronously with the defect portion, to thereby calculate, for example, a total sum of the gradation differences, a total sum of absolute values of the differential values, and the like. The image data of the defect portion and the values obtained at the characteristic quantity calculation unit 508 are collected and supplied to a defect information unit 509. In accordance with the information supplied from the defect information unit 509, a defect classification—analysis unit 510 classifies each defect, and analyzes the fatality judgment of the detected defect, the false information judgement, and the like. Although the defect information may be supplied directly to a host computer 59 under the control of a control CPU 520 and the like, the defect information together with the defect classification and analysis made by the defect classification—analysis unit 510 may be supplied. A defect information holding unit 511 holds the information such as defect image data, defect information, defect classification—analysis results and the like. The defect information held by the defect information holding unit 511 may be supplied, when necessary, to the host computer 59 under the control of the control CPU 520 and the like.

In this embodiment, although a chip comparison process is used illustratively, a cell comparison process may be performed in the similar manner for the case wherein cells having the same structure are regularly disposed such as memory cell mat units. In this case, the position correction is performed by displacing the inspection image by a cell pitch, and the process of detecting a large position displacement between images is not necessary. Depending upon the circuit layout, the CH division unit 503 is not required to divide the inspection image and reference image independently supplied from the chip memory 502, but the image signal before the position correction unit 504 may be divided.

The host computer 59 is provided with an unrepresented GUI (Graphical User Interface) and operates to receive an instruction from an operator and control the whole apparatus. As GUI, an input means such as a display monitor, a keyboard, a mouse and the like of a personal computer is generally used. The control subjects of GUI include: for example, an inspection control unit 601 for controlling an inspection sequence; a defect confirmation control unit 602 for classifying the defect information in accordance with the characteristic quantities after the inspection and confirming the detected defect; a recipe control unit 603 for forming a recipe of the inspection; a utility control unit 604 for controlling utilities necessary for running the apparatus; a defect judgement unit 605 for extracting a real defect from the defect information by a real ghost process or the like; a sequence control unit 606 for controlling the collective operation such as inspection and defect confirmation; a GUI control unit 607; and a data management unit 608 for managing the inspection results, defect images, recipe information and the like.

Figure 2:
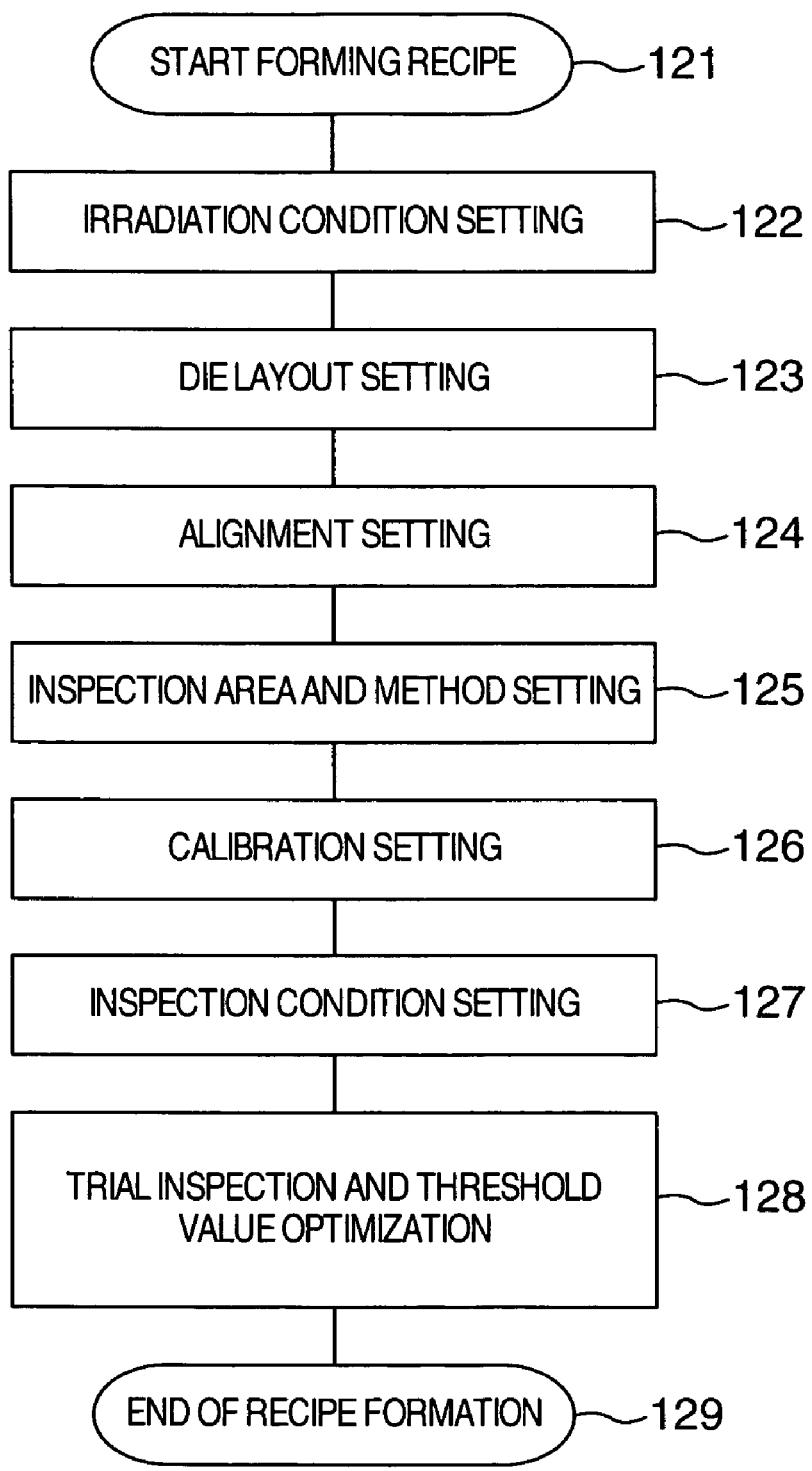
FIG. 2 is a flow chart illustrating the procedure of forming a recipe.

FIG. 2 is a flow chart illustrating the procedure of forming a recipe. The recipe is a menu of parameters necessary for the execution of inspection. Although a variety type of recipe forming procedures may exist, in this embodiment it is assumed that items necessary for the recipe are sequentially set. It is obvious that the set contents can be changed thereafter at any time.

For example, the items to be set to the recipe include irradiation condition setting, die layout setting, alignment setting, inspection area and method setting, calibration setting, inspection condition setting and the like. In the irradiation condition setting 122, the optimum electronic optical conditions are set in order to acquire a SEM image for circuit pattern inspection. In this irradiation condition setting, in addition to the electronic optical system conditions, an inspection pixel size, an image addition number, a SEM image focussing condition and the like are also set. In the die layout setting 123, settings are made as to the layout of dies in an inspection wafer. In the alignment setting 124, a rotation, offset and the like of an inspection wafer are detected so that the inspection apparatus can inspect the desired position in the desired die.

In the inspection area and method setting 125, the inspection area of an inspection wafer and an inspection method are set. In the inspection area setting, it is possible to designate the die to be inspected and the area in the die to be inspected. The inspection area in a die may be a cell comparison area in the area where repetitive patterns such as memory cells are formed. For the die comparison, the die comparison area may be designated. The inspection method indicates whether the designated area is subjected to the cell comparison operation, the die comparison operation, a mixed operation of the cell comparison and die comparison or the like. It is also possible to designate whether the inspection is performed in an X-direction or a Y-direction.

In the calibration setting 126, for example, the position and the like of calibration is set in order to optimize the brightness and contrast of an SEM image. In the inspection condition setting 127, mainly the threshold value for defect detection and the detailed method of the cell comparison and die comparison are designated. In the trial inspection and automatic defect classification condition setting 128, an actual inspection operation is performed to detect a defect and designate the classification condition for automatic defect classification by using the defect information of the detected defect. A wafer inspection recipe is formed by making the above-described settings.

Figure 3:
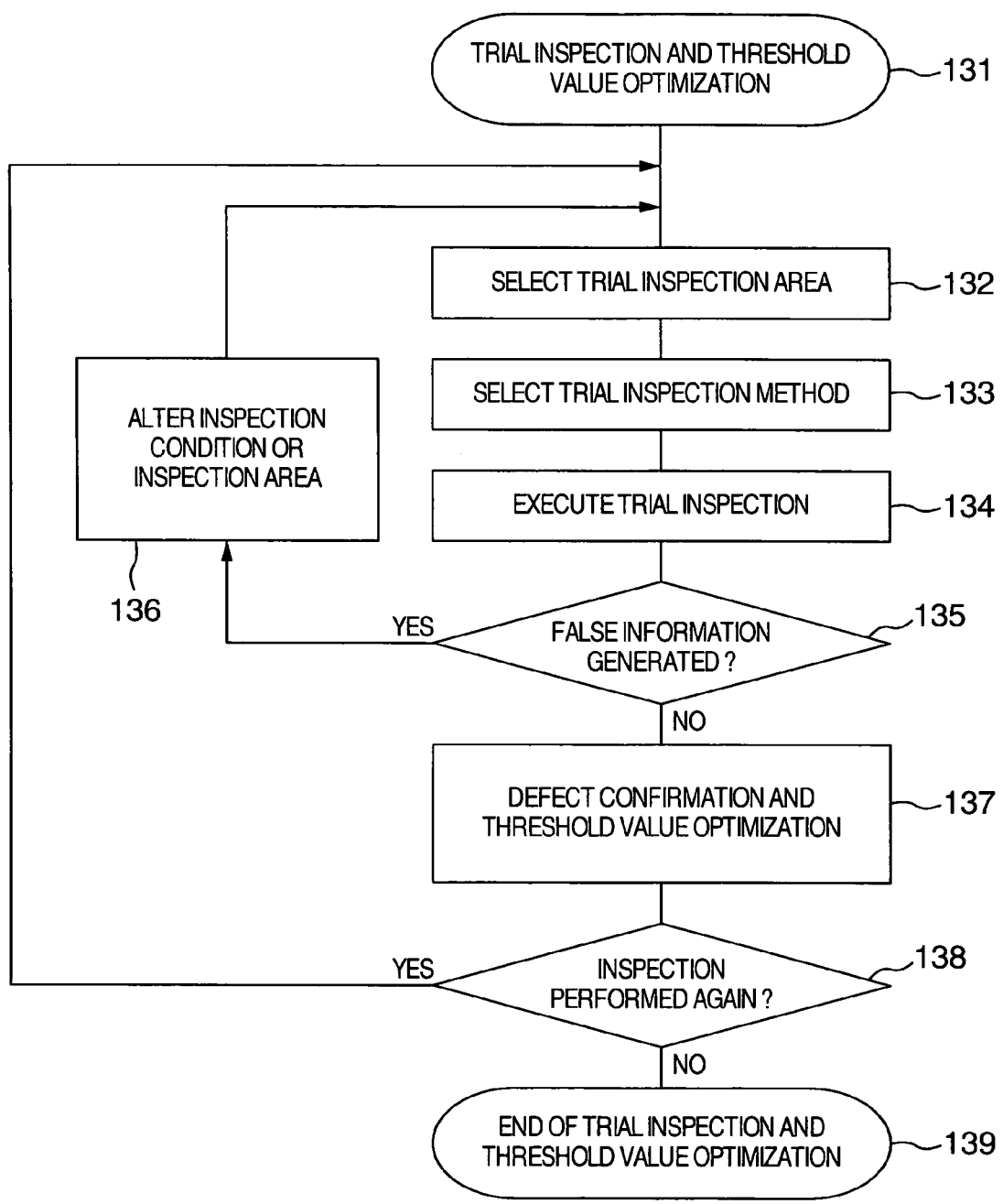
FIG. 3 is a flow chart illustrating the procedure of setting the inspection conditions for trial inspection and automatic defect classification.

FIG. 3 is a flow chart illustrating the procedure of setting the inspection conditions for trial inspection and automatic defect classification. The trial inspection is also used for confirming the inspection conditions previously set such as a threshold value, and if necessary the process returns to the inspection condition setting.

First, the inspection area and inspection method are selected to perform the trial inspection. In this case, the inspection area and method are given the degree of freedom allowing them to be altered irrespective of the previously designated contents, and if the alteration is valid, the inspection area and method are altered. If false information is generated in the trial inspection, the inspection area or method is changed to adjust in such a manner that the inspection can be performed generally in a normal manner. The cause of false information generation may be the case wherein improper inspection conditions are used. For example, if the inspection condition of a low scan beam energy is used, a brightness variation of a pattern is formed because of a charge variation in the specimen, resulting in the false information. The other case is that a non-repetitive pattern is defined as the inspection area for the cell comparison.

If the inspection can be performed generally in a normal manner, the defect confirmation and threshold value optimization are performed. The reliability and effectiveness of the threshold value increases more as the number of samples becomes larger. Therefore, the inspection is performed again if necessary.

Figure 4:
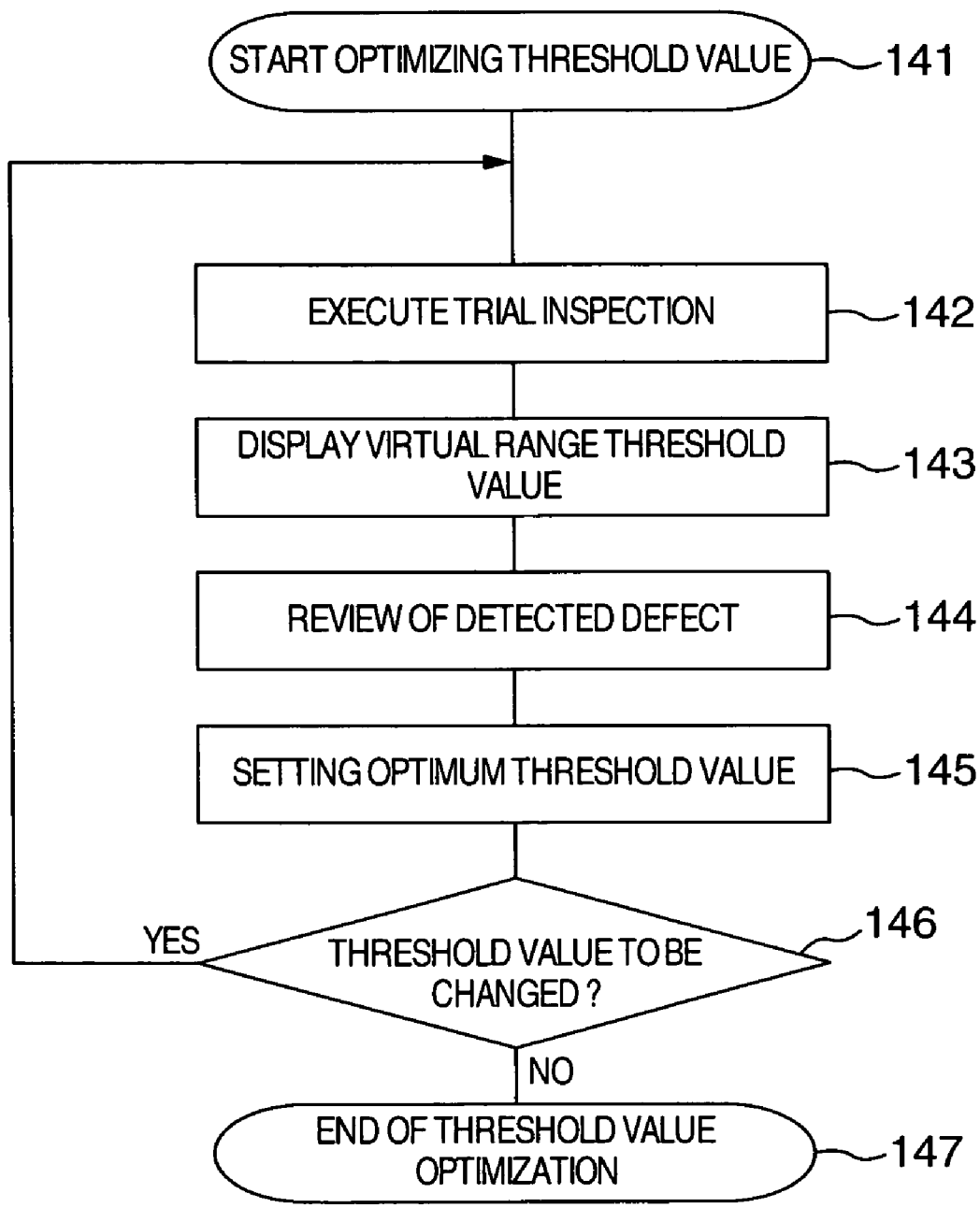
FIG. 4 is a flow chart illustrating the procedure of optimizing a threshold value.

FIG. 4 is a flow chart illustrating the procedure of optimizing the threshold value. There are several methods of determining a threshold value. In this invention, the trial inspection is first performed at a threshold value set lower, and the defect detected by the trial inspection is reviewed by using a virtual range threshold value display. Through this review of the detected defect, the optimum threshold value is obtained in accordance with the virtual threshold value and the detected defect state. The virtual range threshold value is the maximum threshold value capable of detecting a defect and is held as one of the terms of the defect information. The virtual range threshold value display is to select and display the defect information contained in the range designated by GUI in accordance with the virtual threshold value.

FIGS. 5 to 9 are diagrams showing examples of screens displayed on the display monitor. In the embodiment shown in FIG. 5, a defect map portion 902 and a threshold value setting tool portion 903 are displayed in a GUI screen portion 901. In the defect map portion 902, the positions where defects are detected are indicated by a mark such as a circle. In the example shown in FIG. 5, the defect position indicated by a white circle corresponding to the defect excluded by the detected threshold value. In this screen, any one chip in the defect map portion 902 can be designated and enlarged by using a mouse or the like, or the defect information such as the type and size of the defect can be displayed by designating the defect position.

The threshold value setting tool portion 903 is constituted of a defect image data display portion 920, a virtual threshold value select portion 921, operation designation buttons for the tools such as setting, cancel and close. Displayed in the defect image data display portion 920 are a plurality of inspection image portions 930 at the defect positions of the defects other than those indicated by the white circle in the defect map portion 902. In the example shown in FIG. 5, although only six defects are shown, other inspection image portions 930 can be displayed by moving a tool bar.

A plurality of values can be designated in the virtual threshold value select portion 921. For example, these values can be set by using an inspection threshold value setting part 905 indicating an inspection threshold value and first and second range threshold value setting parts 906 and 907 for selecting the defect positions to be displayed in the image data display portion 920. The selected defect positions are displayed superposed upon the defect map by discriminating between the remaining defect positions and display marks. In this manner, a distribution of the designated defect positions can be confirmed.

Figure 5:
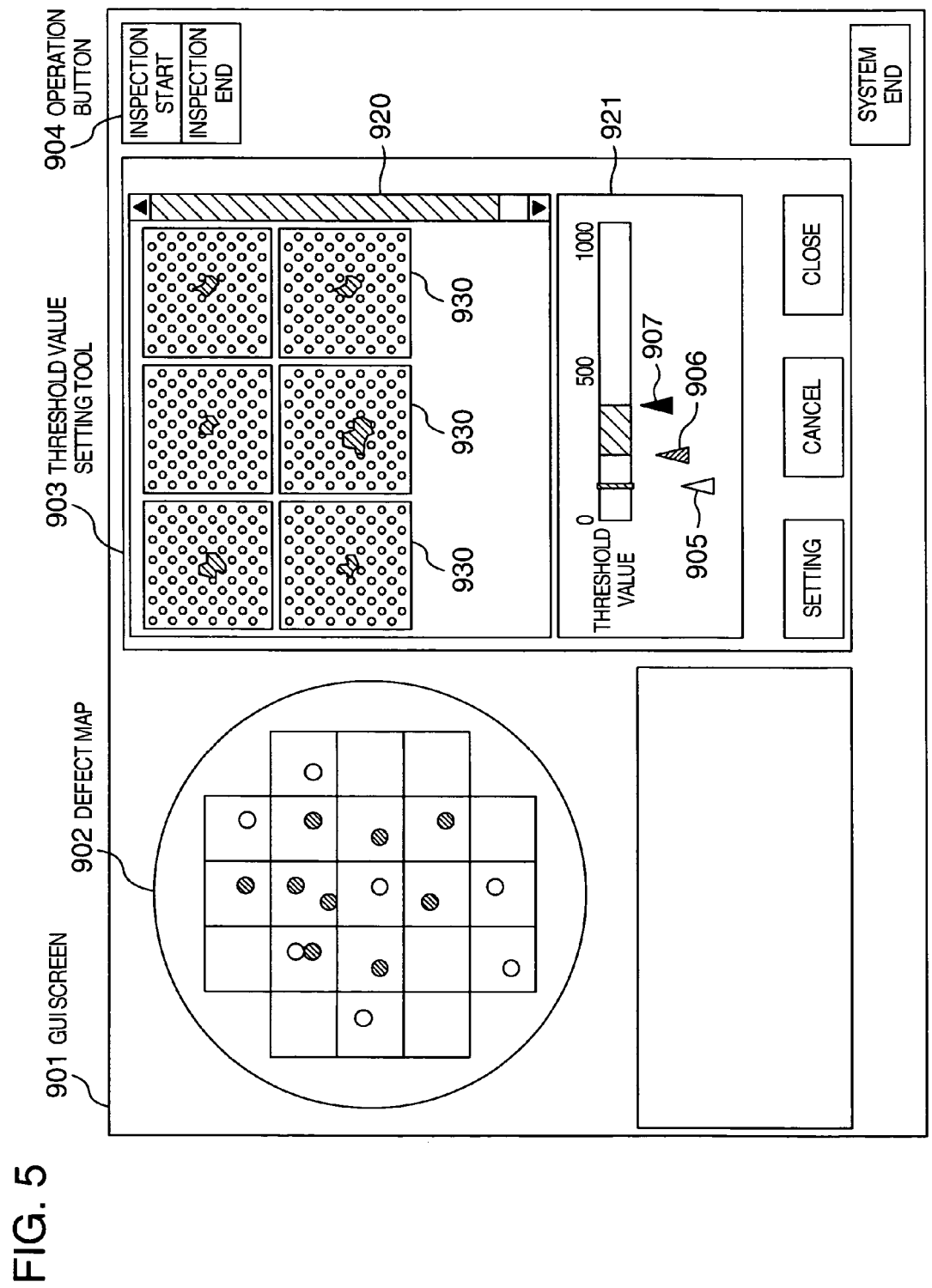
FIG. 5 is a diagram showing an example of a screen displayed on a display monitor.
Figure 6:
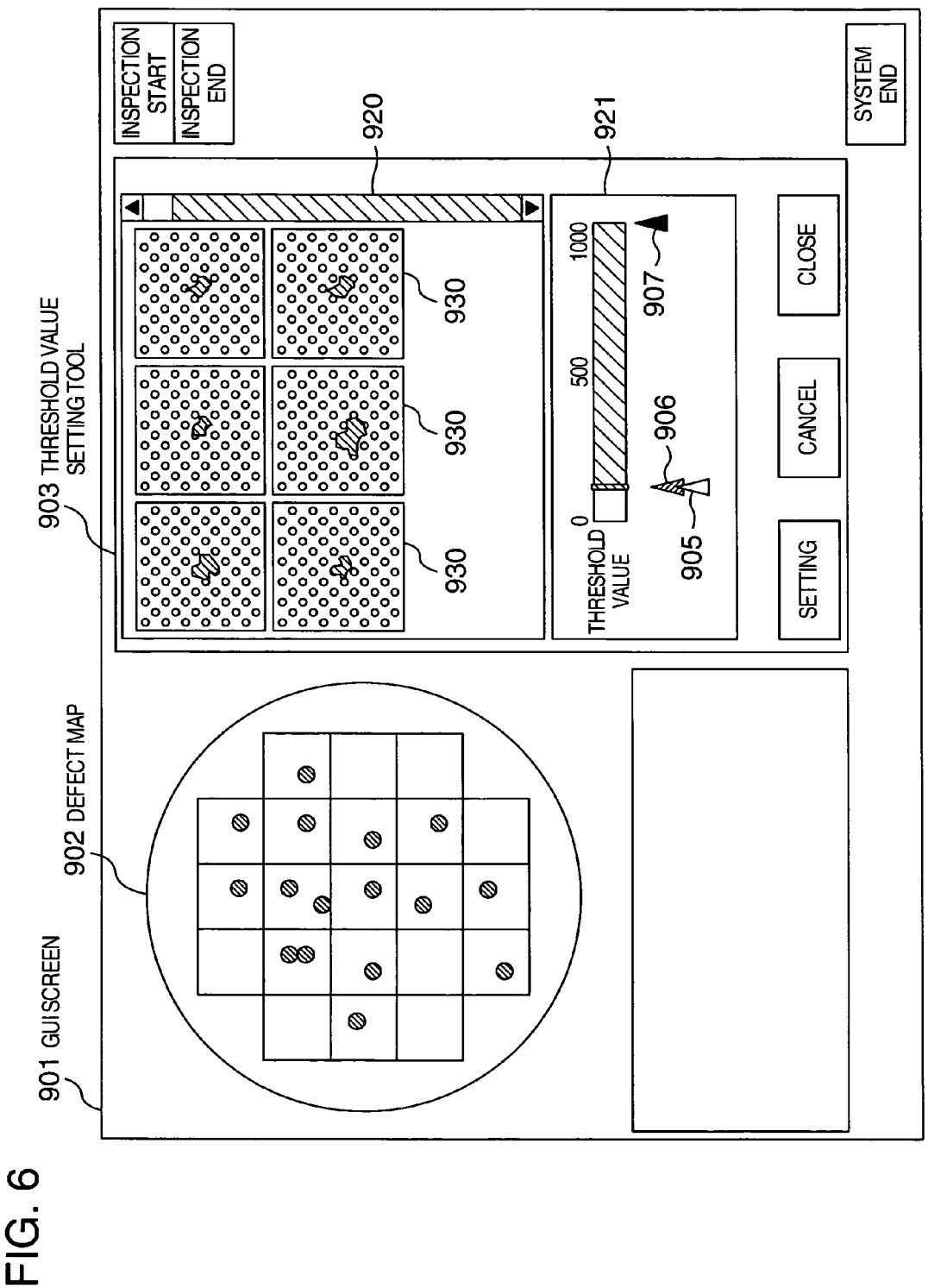
FIG. 6 is a diagram showing another example of a screen displayed on the display monitor.

In the embodiment shown in FIG. 6, the first range threshold value setting part 906 is made coincident with the inspection threshold value setting part 905, and the second range threshold value setting part 907 is made coincident with the upper limit of the threshold value. This state is the initial state when this screen is started up so that defect information of all detected defects can be reviewed. By moving from this screen the first and second range threshold value setting parts 906 and 907 as shown in FIG. 5, it is possible to erase the defect positions indicated by the white circle in the defect map portion 902 or change the display color to thereby discriminate between the defect positions and the excluded defect positions.

Figure 7:
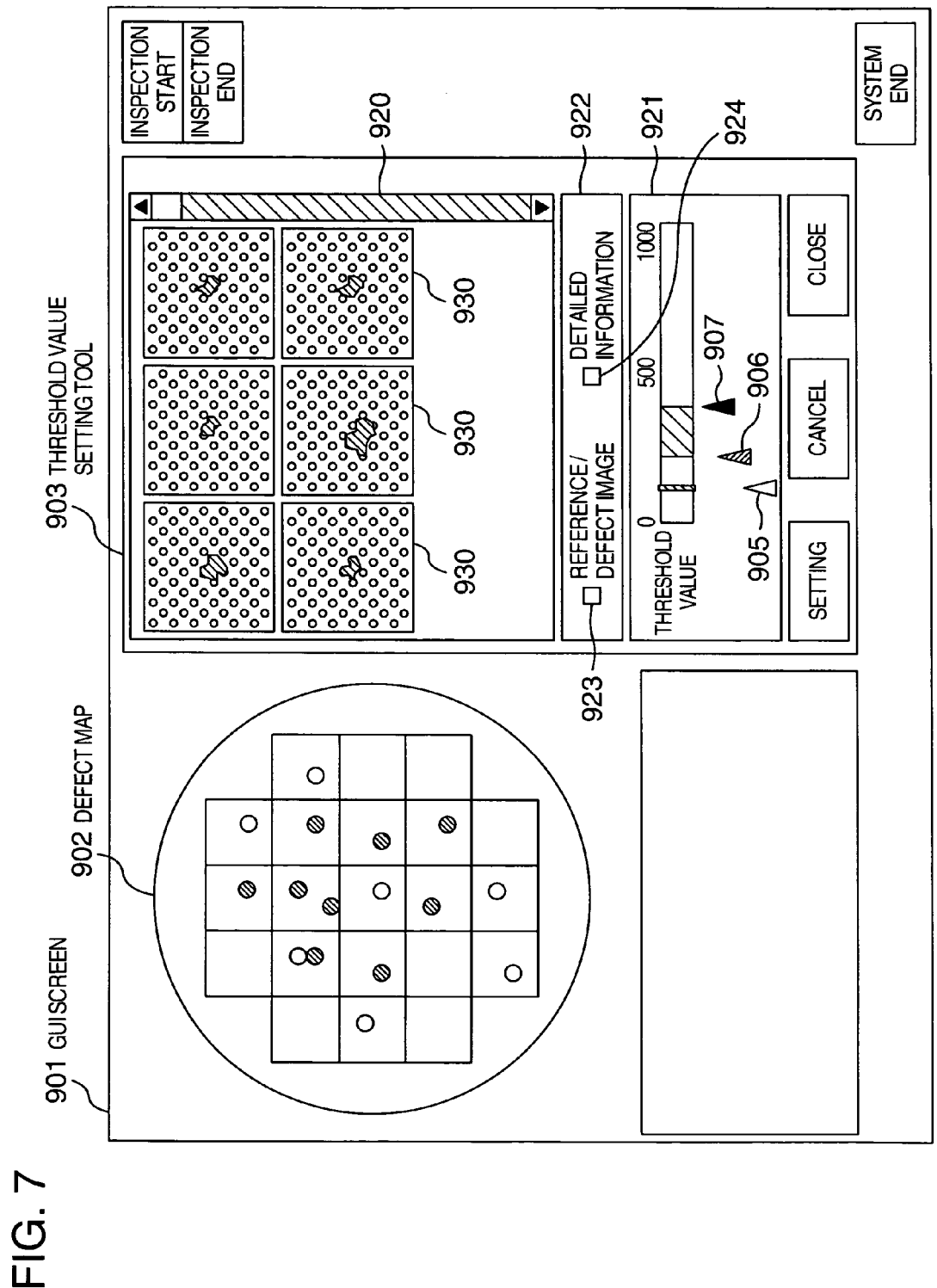
FIG. 7 is a diagram showing another example of a screen displayed on the display monitor.

In the embodiment shown in FIG. 7, a detailed display setting portion is provided as the threshold value setting tool. The detailed display setting portion 922 is provided with a reference/defect image display check button 923 and a detailed information display check button 924. Not only the inspection image but also the reference image and defect image can be displayed in the image data display portion 920.

Figure 8:
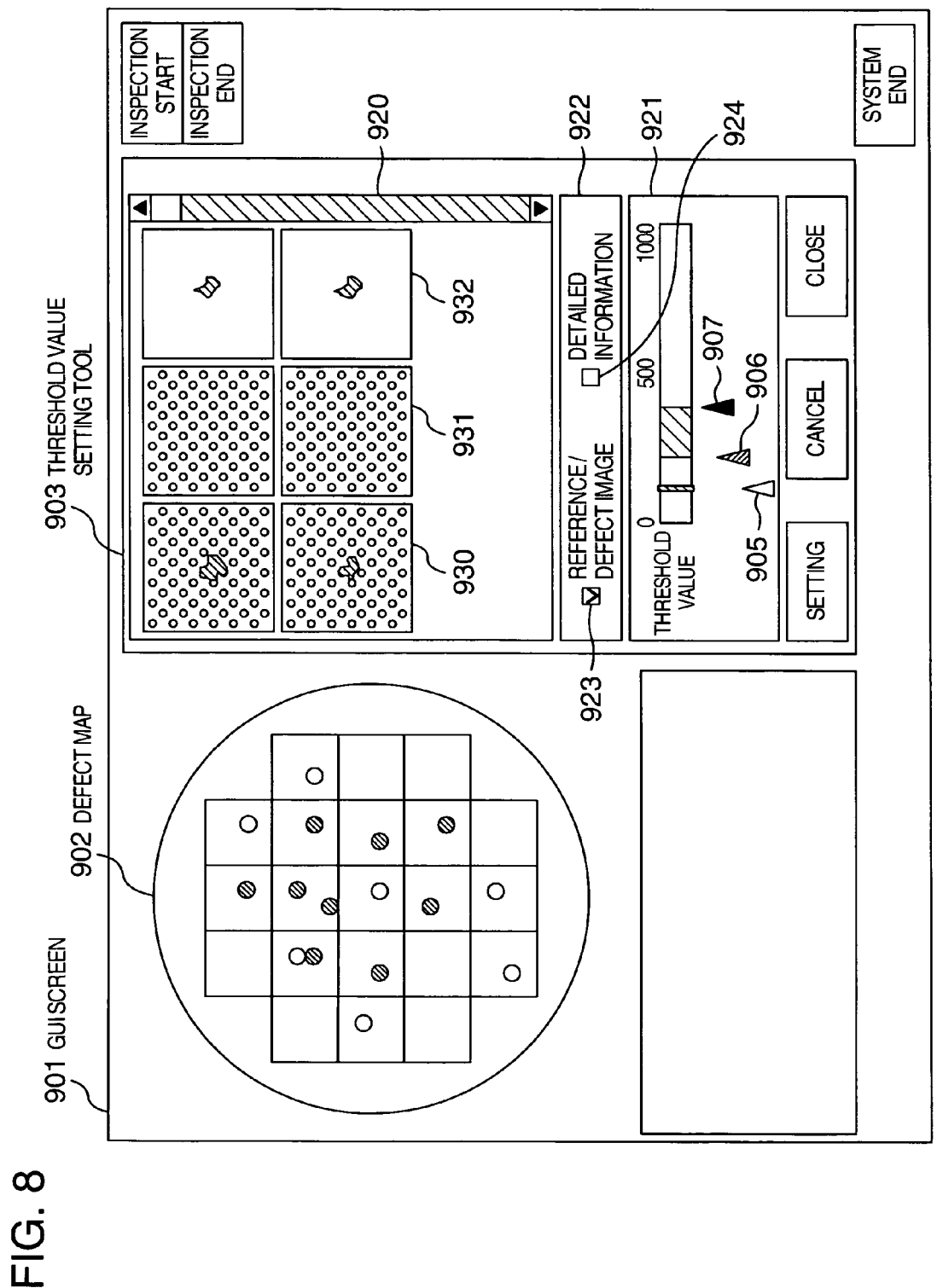
FIG. 8 is a diagram showing another example of a screen displayed on the display monitor.

For example, as shown in FIG. 8, when the reference/defect image display check button 923 is selected, in addition to the inspection image portion 930 at the defect position, a corresponding reference image portion 931 and a corresponding defect image portion 932 are displayed. By disposing these displays side by side, it is possible to correctly review what portion was captured as the defect. In this manner, as the threshold value is changed while the defect is reviewed, unnecessary defects such as false information can be excluded.

Figure 9:
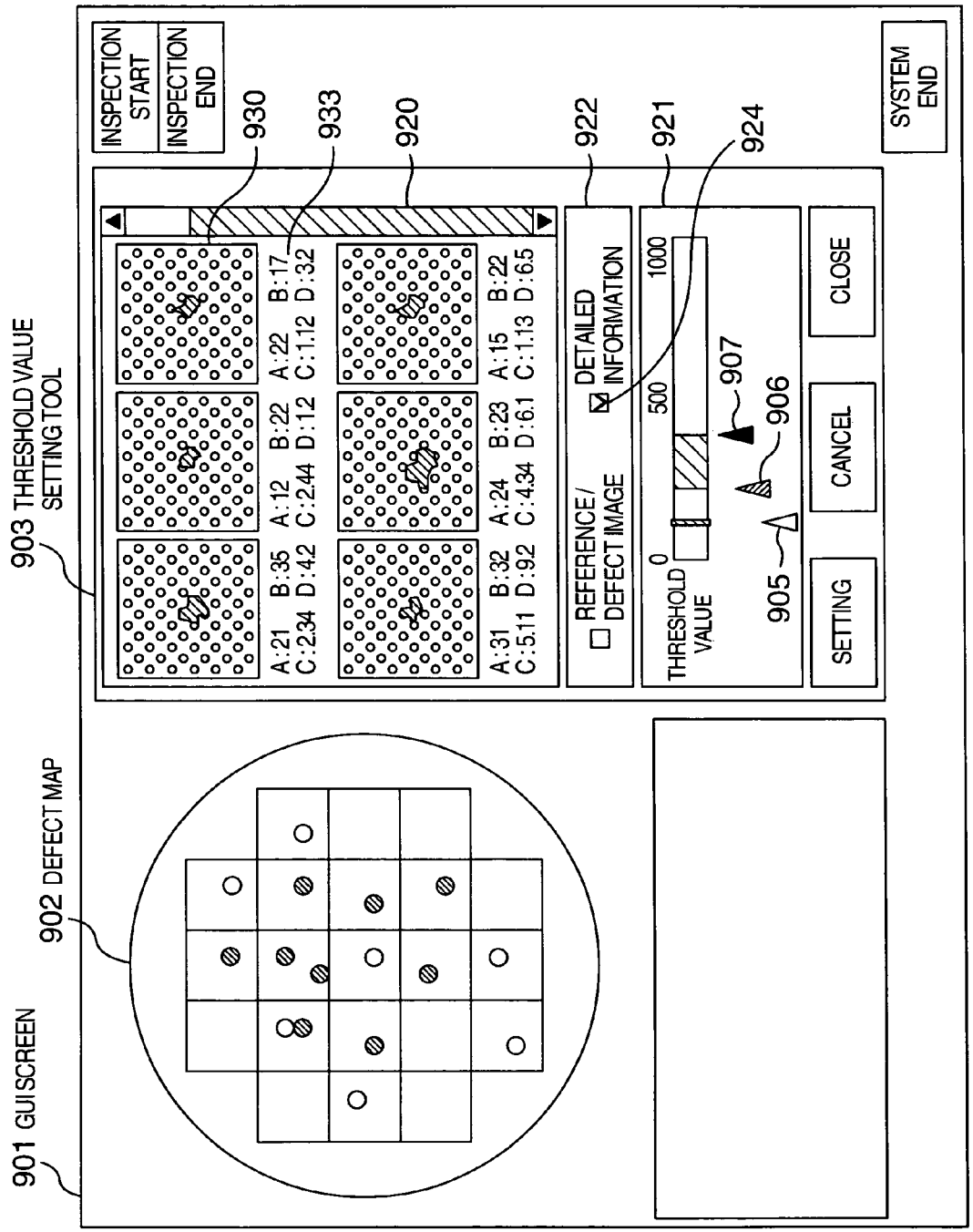
FIG. 9 is a diagram showing another example of a screen displayed on the display monitor.

As shown in FIG. 9, as the detailed information display check button 924 is selected, the detailed information such as the type and size of each defect position is displayed just at the side of the defect image so that the defect can be reviewed in detail along with the defect information.

When both the reference/defect image display check button 923 and detailed information display check button 924 are selected at the same time, the information on the defect position and the reference image and defect image can be displayed at the same time.

As described above, by combining various displays representative of the defect information, the efficiency of defect review can be improved and the efficiency of threshold value setting can be improved so that the recipe can be formed easily.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A circuit pattern inspection method of irradiating an electron beam to a specimen formed with a circuit pattern on a surface thereof, forming an inspection image and a reference image in accordance with a secondary electron of a reflected electron from the specimen, and acquiring an abnormal portion from a comparison of an inspection threshold value with a difference between the inspection image and the reference image, the method comprising steps of:

obtaining a plurality of characteristic quantities of said abnormal portion from an image of said abnormal portion;

storing the plurality of characteristic quantities of said abnormal portion, the inspection image and the reference image of said abnormal portion; and selectively displaying said abnormal portion by changing a virtual threshold value virtually set for said characteristic quantities.

2. A circuit pattern inspection method according to claim 1, wherein said virtual threshold value has at least two virtual threshold values.

3. A circuit pattern inspection method according to claim 1, wherein the inspection image and the reference image of said abnormal portion, and one or a plurality of images of abnormal portions indicating at least a shape of said abnormal portion are displayed at a time.

4. A circuit pattern inspection apparatus for irradiating an electron beam to a specimen formed with a circuit pattern on a surface thereof, forming an inspection image and a reference image in accordance with a secondary electron of a reflected electron from the specimen, and acquiring an abnormal portion from a comparison of an inspection threshold value with a difference between the inspection image and the reference image, the apparatus comprising:

a characteristic quantity calculation unit of obtaining a plurality of characteristic quantities of said abnormal portion from an image of said abnormal portion;

a memory for storing the plurality of characteristic quantities of said abnormal portion, the inspection image and the reference image of said abnormal portion; and a display unit for selectively displaying said abnormal portion by changing a virtual threshold value virtually set for said characteristic quantities.

5. A circuit pattern inspection apparatus according to claim 4, wherein said virtual threshold value has at least two virtual threshold values.

6. A circuit pattern inspection apparatus according to claim 4, wherein the inspection image and the reference image of said abnormal portion, and one or a plurality of images of abnormal portions indicating at least a shape of said abnormal portion are displayed at a time.

* * * * *